United States Patent
Anderson et al.

(10) Patent No.: US 11,225,657 B2
(45) Date of Patent: Jan. 18, 2022

(54) SYNTHETIC AUXOTROPHS WITH LIGAND DEPENDENT ESSENTIAL GENES FOR BIOSAFETY

(71) Applicant: THE REGENTS OF THE UNIVERSITY OF CALIFORNIA, Oakland, CA (US)

(72) Inventors: John C. Anderson, Berkeley, CA (US); Gabriel Lopez, Altadena, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 776 days.

(21) Appl. No.: 15/823,238

(22) Filed: Nov. 27, 2017

(65) Prior Publication Data

US 2018/0155711 A1 Jun. 7, 2018

Related U.S. Application Data

(63) Continuation of application No. PCT/US2016/034889, filed on May 27, 2016.

(60) Provisional application No. 62/167,854, filed on May 28, 2015.

(51) Int. Cl.
| | |
|---|---|
| *C12N 15/10* | (2006.01) |
| *C12N 1/20* | (2006.01) |
| *C12N 1/36* | (2006.01) |
| *C12N 15/52* | (2006.01) |

(52) U.S. Cl.
CPC ........... *C12N 15/1079* (2013.01); *C12N 1/20* (2013.01); *C12N 1/36* (2013.01); *C12N 15/1027* (2013.01); *C12N 15/1031* (2013.01); *C12N 15/1058* (2013.01); *C12N 15/1093* (2013.01); *C12N 15/52* (2013.01)

(58) Field of Classification Search
None
See application file for complete search history.

(56) References Cited

U.S. PATENT DOCUMENTS

| | | |
|---|---|---|
| 6,410,245 B1 | 6/2002 | Northrop |
| 2005/0272072 A1 | 12/2005 | Liu et al. |
| 2006/0211046 A1 | 9/2006 | Wood |

FOREIGN PATENT DOCUMENTS

| | | |
|---|---|---|
| JP | 2011055721 A | 3/2011 |

OTHER PUBLICATIONS

Kianmajd et al., Transfer-to-Excellence Research Experiences for Undergraduates Program (Year: 2013), http://e3s-center.berkely.edu/education-diversity/education/undergraduate/tte-transfer-excellence-summer-research-program/tte-program-archive-b/2013-2/.*
Taylor et al., "Engineering an allosteric transcription factor to respond to new ligands" 13(2) Nature Methods 177-183, Methods ( Year: 2015).*
Mandell, Daniel J. et al., "Biocontainment of genetically modified organisms by synthetic protein design", Nature, vol. 518, No. 7537, Feb. 5, 2015, pp. 55-60.
Rovner, Alexis J. et al., "Recoded organisms engineered to depend on synthetic amino acids", Nature, vol. 518, vol. 7537, Jan. 21, 2015, pp. 89-93.
Guo, Zhihong. et al., "Designing Small-Molecule Switches for Protein-Protein Interactions", Science, vol. 288, Jun. 16, 2000, pp. 2042-2045.
Medema, Marnix H. et al., "Computational tools for the synthetic design of biochemical pathways", Nature Reviews Microbiology, vol. 10, No. 3, Mar. 2012, pp. 191-202, published online Jan. 23, 2012.
Quandt, Erik M. et al., "Decafeination and Measurement of Caffeine Content by Addicted *Escherichia coli* with a Refactored N-Demethylation Operon from Pseudomonas putida CBB5", ACS Synthetic Biology, American Chemical Society, vol. 2, Mar. 8, 2013, pp. 301-307.
European Patent Office (EPO), Communication (extended European search report) dated Oct. 29, 2018, related European patent application No. 16800848.0, pp. 1-6, claims searched, pp. 7-10.
Dagliyan, Onur et al., "Rational design of a ligand-controlled protein conformational switch", PNAS, 2013, vol. 110, No. 17, pp. 6800-6804, Apr. 23, 2013.
Japan Patent Office (JPO), official action dated Feb. 18, 2020, related Japanese patent application No. 2017-560703, pp. 1-14, English-language translation, pp. 15-31, claims examined, pp. 32-36.
European Patent Office (EPO), Communication pursuant to Article 94(3) EPC dated Apr. 30, 2020, related European patent application No. 16800848.0, pp. 1-5, claims examined, pp. 6-8.
Cai, Yizhi et al., "Intrinsic biocontainment: multiplex genome safeguards combine transcriptional and recombinational control of essential yeast genes", PNAS, vol. 112, No. 6, Feb. 10, 2015, pp. 1803-1808.

(Continued)

*Primary Examiner* — Nancy J Leith
(74) *Attorney, Agent, or Firm* — O'Banion & Ritchey LLP; John P. O'Banion

(57) ABSTRACT

Synthetic auxotrophs with one or more ligand-dependent essential gene functions and methods of production that can be used for biosafety. The ligand-dependent function of an essential gene product can be produced by a series of mutations in the ORF of an essential gene; N, C, or insertional fusions of ligand-binding domains with essential genes or an engineered ligand-dependent intein splicing to alter essential gene function. A positive and/or negative selection can be used to identify auxotrophs from created mutant libraries. The positive selection is performed by growing a mutant library in conditions where growth or viability depends on the function of mutagenized essential genes. The negative selection eliminates constitutively growing cells that do not require a ligand for growth by growing the library in the absence of complementing ligand and in conditions where growing cells are eliminated. Desirable phenotypes are collected after the selections.

8 Claims, 5 Drawing Sheets

(56) References Cited

OTHER PUBLICATIONS

Kianmajd, Fariba et al., "Characterization of Tetracycline Inducible Orn Strain UM431", 2013 Transfer-to-Excellence Research Experiences for Undergraduates Program (TTE REU Program), University of California, Berkeley, Sep. 2013, 2 pages.
Korean Intellectual Property Office (KIPO), International Search Report and Written Opinion dated Aug. 25, 2016, counterpart PCT international application No. PCT/US2016/034889, pp. 1-13, with claims searched, pp. 14-18.
Lopez, Gabriel et al., "Synthetic Auxotrophs with Ligand-Dependent Essential Genes for BL21(DE3) Biosafety Strain", ACS Synthetic Biology, Epub., vol. 4, No. 12, Jun. 15, 2015, pp. 1279-1286.
Japan Patent Office (JPO), official action dated Dec. 22, 2020, related Japanese patent application No. 2017-560703, pp. 1-6, English-language translation, pp. 7-13, claims examined, pp. 14-18.
European Patent Office (EPO), Communication pursuant to Article 94(3) EPC dated Jan. 28, 2021, related European patent application No. 16800848.0, pp. 1-5, claims examined, pp. 10-19.

\* cited by examiner

SYNTHETIC AUXOTROPHS WITH LIGAND DEPENDENT ESSENTIAL GENES FOR BIOSAFETY

CROSS-REFERENCE TO RELATED APPLICATIONS

This application is a 35 U.S.C. § 111(a) continuation of PCT international application number PCT/US2016/034889 filed on May 27, 2016, incorporated herein by reference in its entirety, which claims priority to, and the benefit of, U.S. provisional patent application Ser. No. 62/167,854 filed on May 28, 2015, incorporated herein by reference in its entirety. Priority is claimed to each of the foregoing applications.

The above-referenced PCT international application was published as PCT International Publication No. WO 2016/191757 on Dec. 1, 2016, which publication is incorporated herein by reference in its entirety.

STATEMENT REGARDING FEDERALLY SPONSORED RESEARCH OR DEVELOPMENT

This invention was made with Government support under 1151220, awarded by the National Science Foundation. The Government has certain rights in the invention.

INCORPORATION-BY-REFERENCE OF COMPUTER PROGRAM APPENDIX

Not Applicable

BACKGROUND

1. Technical Field

The present technology pertains generally to organisms genetically engineered for controlled biocontainment, and more particularly to synthetic auxotrophs with ligand-dependent essential genes and methods of fabrication.

2. Background Discussion

Biotechnology depends heavily on the creation of genetically engineered organisms for basic research as well as industrial scale production of materials. The inherent strengths of biology, limitless design complexity, and self-replication also draw scrutiny from people concerned that engineered organisms might escape. These self-replicating re-engineered cells may produce undesirable consequences if they escape or are allowed to overwhelm their natural ecosystems.

Biocontainment is a set of strategies that are used to contain pathogenic and genetically modified organisms to the laboratory that includes both physical barriers and genetic modifications to the organism to ensure that the engineered organisms remain under complete control. Biocontainment is needed to prevent unintended proliferation of genetically modified organisms in a wide variety of medical, agricultural, research and synthetic biology operations.

Genetic biocontainment strategies are typically centered on the formation of auxotrophic mutations or inducible lethality. Conventional approaches include the use of conditional mutants such as temperature or pH or osmolarity sensitive mutants that can be eliminated with a change of an environmental condition. Similarly, metabolic bio-containment strategies depend on a mutation of a single cellular metabolic mechanism that relies on supplementation of a specific nutrient such as an amino acid to keep the engineered microbe alive. Other approaches of inducible lethality include the insertion of suicide genes or plasmids in bacteria based on toxins.

However, existing genetic biocontainment methods are often not effective because the imposed genetic barrier mechanisms can be circumvented through spontaneous mutagenesis, horizontal gene transfer or by scavenging environmentally available compounds to overcome the metabolic deficiency.

In addition, current genetic containment approaches lack redundancy and the frequency of escape mutants from single mutations make the genetic barriers placed on the organism to prevent it from entering the environment insufficient. Furthermore, toxin genes may be leaky reducing the fitness of the organism making them unsatisfactory for industrial applications or in research settings.

Therefore, there remains an urgent need to develop more effective approaches for to prevent the unintended proliferation of such organisms in natural ecosystems and public exposure to modified pathogenic organisms. The present technology satisfies these needs and is generally an improvement in the art.

BRIEF SUMMARY

The present technology provides ligand-dependent synthetic auxotroph organisms that are engineered to depend on at least one particular ligand molecule for their viability. Generating ligand-dependence in an essential gene results in an organism requiring that ligand to survive. This is a simple approach for developing synthetic auxotrophs. These organisms might be used as a biosensor to identify new enzymatic activities from large DNA libraries. They can also be used in a biocontainment strategy by confining genetically modified organisms to the lab or industrial scale systems. This intrinsic form of biological containment may also enable deployment of engineered organisms for bioremediation, environmental monitoring, or cell therapy applications.

Conventional metabolic auxotrophs are typically created by deleting or knocking out a gene removing the ability of an organism to make an amino acid or other metabolite so that the amino acid must be supplied exogenously. This is a genetic system level modification that is limited to the set of chemicals that already exist within the metabolism of the organism.

However, instead of deleting or knocking out genes to make auxotrophs, the present technology modifies essential gene products such as proteins to be ligand dependent which essentially provides an allosteric control over the function of essential genes. Instead of a genetic system level modification for auxotrophy, the present technology takes a protein engineering approach to generate functional dependence of an essential gene product on some molecule such as benzothiazole that is not a natural part of the metabolism of the organism.

Although the modifications are normally at the protein level, the ligand-dependency is manifest at the genetic system level. Consequently, the generation of synthetic auxotrophs is different and superior because the methods are not limited to metabolic genes and can target much more vital things like DNA replication or some other essential cellular process.

The methods are not limited to the use of molecules that are part of the natural metabolism of the organism and systems that can be bypassed by the organism. Rather new ligand-dependent metabolic or cellular function requirements can be imposed on one or more essential genes. Removal of the ligand will result in either cell death or no growth or other specific ligand-dependent cellular activity.

To produce synthetic auxotrophs with engineered ligand-dependent control over essential genes, essential gene mutant libraries are generated. An engineered organism's viability is contingent on the proper function of its essential genes. A mutant library on an essential gene will result in a set of organisms whose growth is tied to the function of the mutant essential gene. Since ligand-dependent protein function can be identified from essential gene libraries, large, combinatorial libraries containing many ligand-dependent phenotypes are produced. The library of essential gene variants is preferably generated, using any of the following, individually or in combination: 1) Random or targeted mutagenesis on the open reading frame of the essential gene, for example; 2) Using N, C, or insertional fusions of ligand-binding domains with the essential gene; or 3) Using/engineering ligand-dependent intein splicing to alter essential gene function.

The generated naïve essential gene libraries contain organisms of three basic phenotypes: viable mutant strains with functional essential genes, lethal mutant strains with non-functional essential genes, and ligand-dependent mutant strains with ligand-dependent essential genes.

In order to isolate ligand-dependant strains, the essential gene libraries are preferably passed through a dual selection consisting of a positive selection based on chemically-complemented growth and a negative selection. Survivors of the dual selection can then be multiplied and then screened for the desired phenotype.

Synthetic auxotrophs with several essential genes that are dependent on a single ligand can be designed that will exhibit exceptionally small escape frequencies that are reduced by the number of essential genes involved. In addition, ligand-dependent synthetic auxotrophs that are dependent on more than one different ligand can also be designed. Existing metabolic auxotrophs, such as temperature dependent or amino acid dependent organisms, can also be engineered to be ligand-dependent to provide parallel controls over the organism.

According to one aspect of the technology, a synthetic auxotroph with one or more ligand-dependent essential genes is provided where essential gene function or growth is controlled by the presence of the ligand.

Another aspect of the technology is to provide a method of producing a synthetic auxotroph where ligand-dependent function of an essential gene product is the result of a series of mutations in the ORF of an essential gene, resulting in post-translational, ligand-dependent function of the essential gene product.

Another aspect of the technology is to provide a method of producing a synthetic auxotroph where ligand-dependent function of an essential gene product is the result of a ligand-binding domain (LBD) that is N or C-terminally fused or inserted to the essential gene product, where the ligand-binding domain is capable of controlling essential gene product function.

A further aspect of the technology is to provide a method of producing a synthetic auxotroph where ligand-dependent function of an essential gene product is the result of a ligand-dependent intein inserted into an essential gene such that the unspliced fusion protein is inactive, but upon ligand-mediate intein splicing, a functional protein is produced.

Another aspect of the technology is to provide a method of producing a synthetic auxotroph where a positive and/or negative selection is used (if available) to identify synthetic auxotrophs.

Another aspect of the technology is to provide genetically engineered organisms that are not a risk to the environment upon accidental release because the essential genes need to be "turned on" for survival or growth by a ligand that is not naturally occurring or normally available in the environment.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

Referring more specifically to the drawings, for illustrative purposes, embodiments of the methods and resulting structures are generally shown. Several embodiments of the technology are described generally in FIG. 1A through FIG. 5 to illustrate the synthetic auxotrophs and fabrication methods. It will be appreciated that the methods may vary as to the specific steps and sequence and the apparatus may vary as to structural details without departing from the basic concepts as disclosed herein. The method steps are merely exemplary of the order that these steps may occur. The steps may occur in any order that is desired, such that it still performs the goals of the claimed technology.

Figure 1:
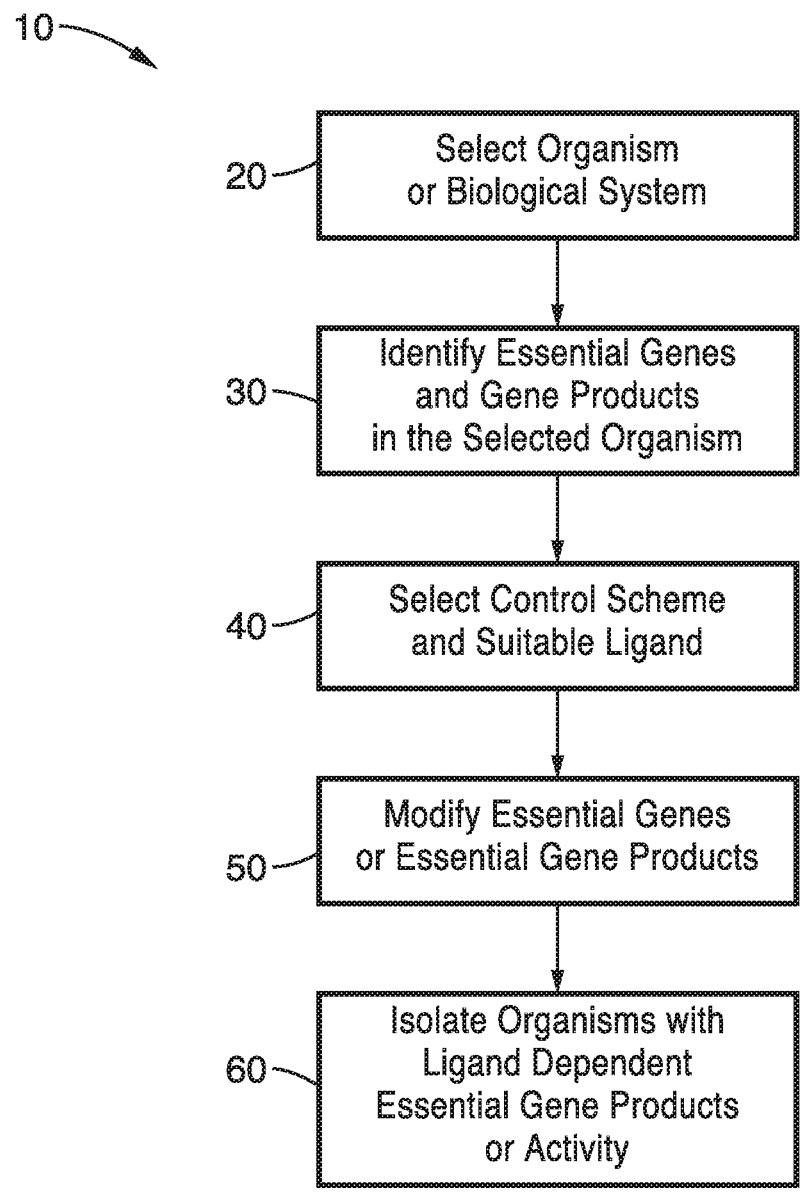
FIG. 1 is a functional flow diagram of a method for producing ligand dependent synthetic auxotrophs according to one embodiment of the technology.

Turning now to FIG. 1, one preferred embodiment of a method 10 for engineering synthetic auxotrophs with at least one ligand-dependent essential gene according to the technology is shown to illustrate one method. At block 20 of FIG. 1, the organism or biological system is selected. The synthetic auxotroph that can be produced by the methods can be based on essentially any suitable organism or biological system. For example bacteria such as actinobacteria, bacteroidetes, cyanobacteria, firmicutes, proteobacteria and others can be used. There are multiple routes to impose synthetic auxotrophy on these organisms.

The methods can also be used with commensal organisms such as human commensal microbes, plant commensal microbes and animal commensal microbes. Single celled eukaryotes (e.g. yeast, immune cells, stem cells, protists) and multicellular eukaryotes (e.g. animals, plants, fungi) can also be selected at block 20 of FIG. 1. Non-living biological systems (i.e. viruses, diagnostics reagents) as well as engineered probiotics, and other therapeutic organisms can also be selected.

Essential genes or gene products of the organisms selected at block 20 are identified for manipulation at block 30 of FIG. 1. This selection is typically identifies genes that are essential for cell growth, vitality or of a specific cellular function.

The control scheme and suitable ligands are determined at block 40 for the targeted essential genes determined at block 30. For example, ligand binding domain insertions or fusions with essential genes to make ligand-dependent essential genes is one approach that can be selected. Here previously identified homologs can be used to guide development of novel variants in new organisms.

Another way to generate is the production of a ligand-dependent intein that is inserted into the essential genes of the target organisms. With the presence of the ligand, splicing occurs and essential genes are functional. Without the ligand, splicing does not occur and essential genes are not functional. Because of the lack of selection schemes in higher organisms, ligand-binding domain insertions/fusions or ligand-dependent intein splicing can be the most effective means of generating ligand-dependent essential genes in these organisms.

The function of ligand-dependent control modules can also be tested in yeast in order to generate information for structure guided modification of essential genes in other eukaryotes (i.e. If a synthetic auxotroph can be created by a LBD fused to essential gene dnaN of yeast, then, given the high degree of structural homology between higher organisms (and especially among essential genes) it is likely that a similar fusion with the same LBD and essential gene dnaN of a human immune T-cell would yield a synthetic auxotroph.

The ligands identified at block 40 will be influenced by the organism, essential gene and control schemes that are selected. However, there are many types of ligands that can be selected at block 40. For example, ligand-dependent essential genes (based on any of the architectures described above) may be controlled by ligands such as molecules that are generally recognized as safe or otherwise considered safe for human consumption (artificial sweeteners, flavors, food ingredients, preservatives, stabilizers, etc.).

Likewise, over the counter drugs, prescription drugs, or illegal narcotic molecules (e.g. ibuprofen, acetaminophen, valium, oxycotin, morphine, cocaine, heroin) may also be candidates. Commodity or specialty chemicals like plastic precursors, pesticides, explosives, flavors, fragrances, dyes, fuels, fertilizers, etc.) can be used.

In addition, small peptide or peptide-like molecules such as hormones, biologic drugs as well as large proteins (i.e. antibodies, disease markers, allergens, etc. . . . ) are available for use.

Complementing ligands and control scheme that is selected at block 40 can be exogenously supplied (i.e. in the case where the organism is kept alive by intentional addition of ligand to growth conditions so that the relevant organism can perform an intended task). In another embodiment the complementing ligand scheme has the ligands provided endogenously.

At block 50 of FIG. 1, the essential genes are modified to be ligand-dependent essential genes using selected medication schemes to impose synthetic auxotrophy (i.e. ligand-dependent inteins etc).

The produced auxotrophs at block 50 are isolated and classified at block 60 and put to use. For example, the isolated organisms may be designed to survive only if they harbor genetic material coding for enzyme that produces the complementing ligand. A library of enzyme mutants could be transformed into the synthetic auxotroph, but only enzymes that make the complementing ligand will survive. By creating ligand-dependent essential genes that require various valuable small molecules, the synthetic auxotrophs can be a powerful biosensing and selection tool for generating novel enzymatic chemistries.

In another embodiment, the organism may be designed to only survive if it harbors genetic material coding for a globular protein that specifically interacts with the ligand-dependent essential genes in order to activate them. This would most likely use a domain-based approach to ligand-dependent essential genes. The protein domains identified here would then be used in a different application (i.e. diagnostics, biologic drugs).

If a selection is available and necessary (depending on library size), it can be used at block 60 to reduce library size. Otherwise, individual mutants can be screened directly for ligand-dependent growth by replica plating (inspecting growth of individual mutants with complementing ligand and without complementing ligand). Other screens include automated colony picking, followed by replica spotting and deep sequencing. In this case the library is grown with the ligand and without the ligand and then deep sequencing is used to count occurrences of each library member in different growth conditions.

Although a single ligand-dependence of a single essential gene is illustrated in FIG. 1, multiple ligand-dependent essential genes can be used to increase the robustness of ligand-dependency. For example, it has been shown that combining multiple ligand-dependent essential genes can dramatically improve the evolutionary stability of synthetic auxotrophy. Multiple ligand-dependencies appear to have up to a multiplicative decrease in escape frequency. In other words, if ligand-dependent essential genes A and B both have individual escape frequencies of 1E-6, then an organism harboring ligand-dependent versions of both A and B should have an escape frequency of 1E-6*1E-6=1E-12.

Systems dependent on multiple ligands can also be designed as well. In addition to designing synthetic auxotrophs with several ligand-dependent essential gene that requires the same complementing ligand, different ligand-dependent essential genes requiring different complementing ligands could be used if a "password" application is desired. More than one ligand is needed for these engineered organisms to survive or to produce some cellular activity.

Figure 2:
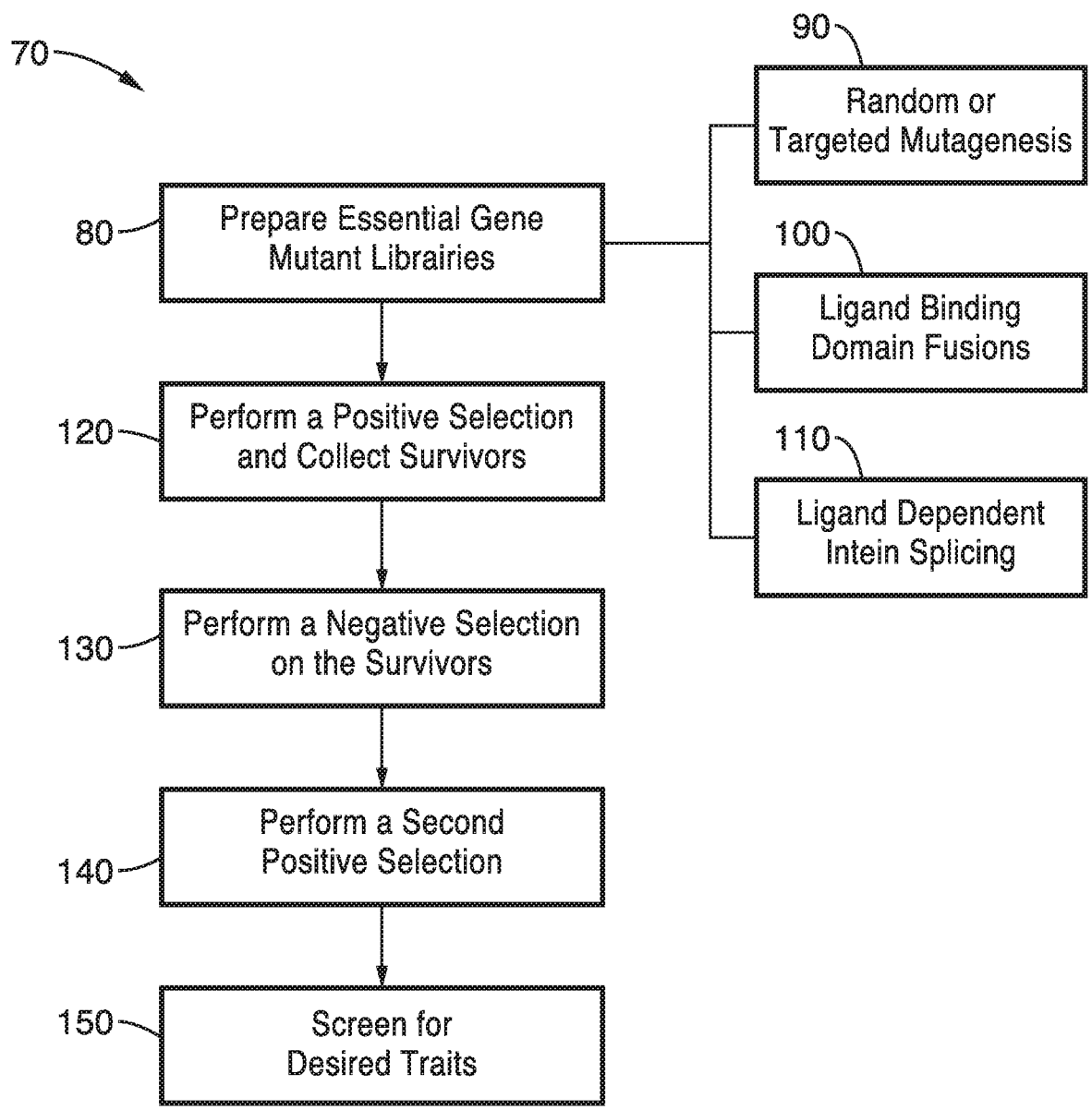
FIG. 2 is a functional flow diagram of a method for producing ligand dependent synthetic auxotrophs with positive and negative screening according to one embodiment of the technology.
Figure 3:
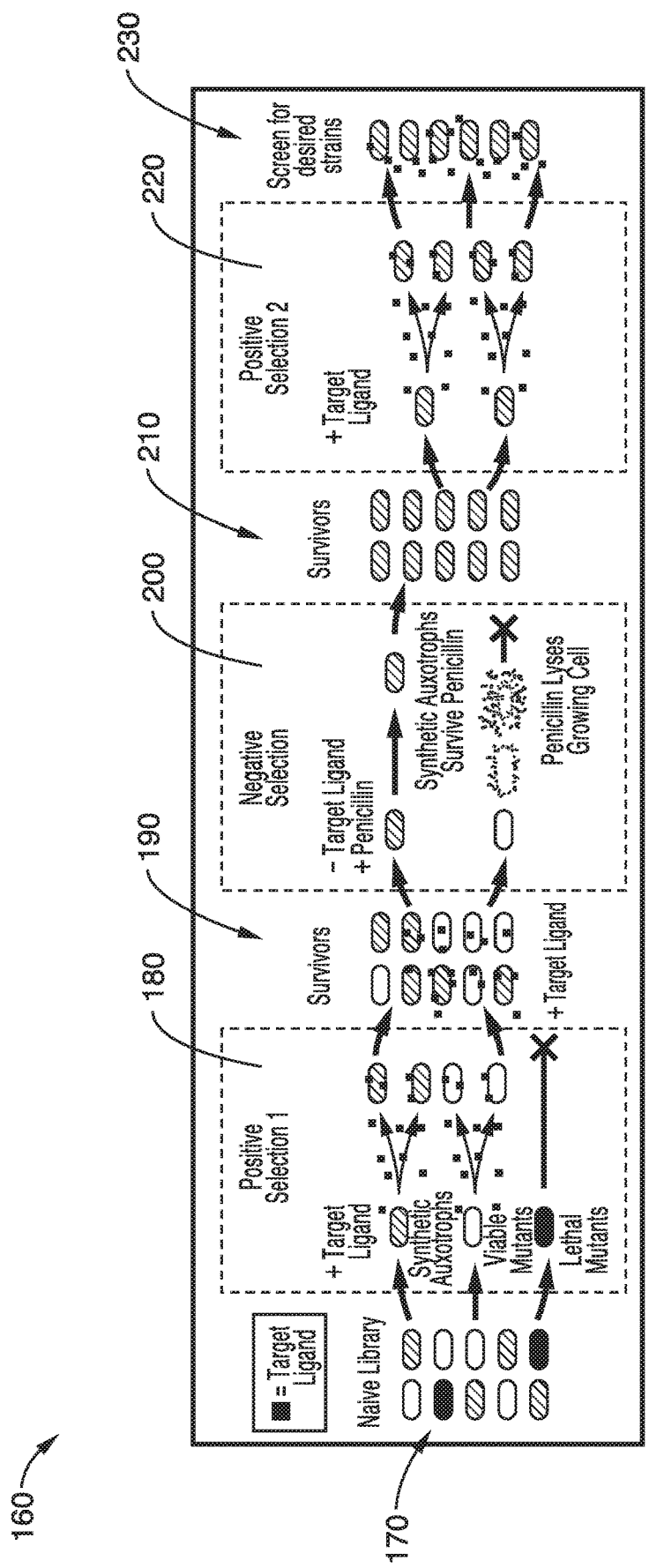
FIG. 3 is a schematic process diagram showing the positive and negative selection steps to screen for ligand dependent bacteria with an antibiotic according to one fabrication method.
Figure 4:
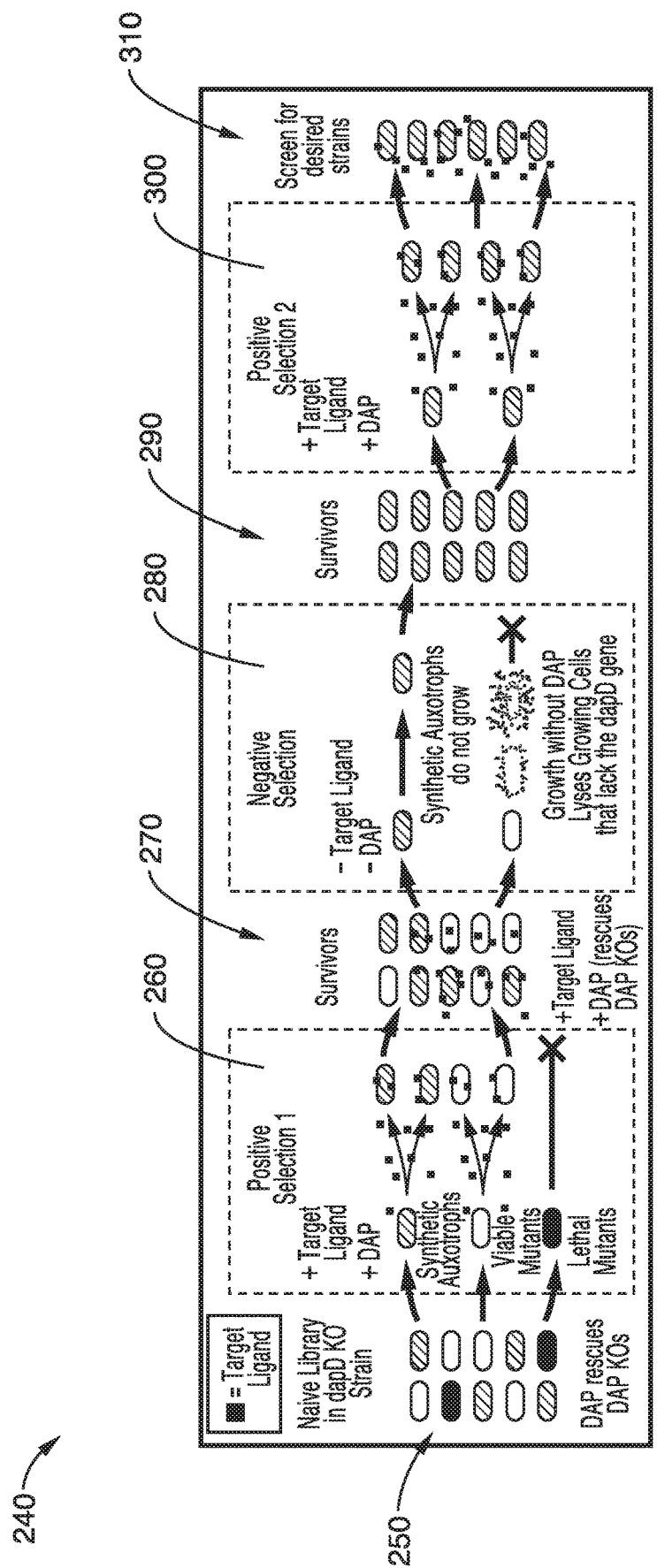
FIG. 4 is a schematic process diagram showing the positive and negative selection steps to screen for ligand dependent bacteria with an according to another embodiment of the fabrication method.

Referring now to FIG. 2 through FIG. 4, one embodiment of the method 70 for engineering a synthetic auxotroph based on one or more ligand-dependent essential genes is shown schematically. At block 80 of FIG. 2, libraries of essential gene mutants are assembled. Essential gene mutant libraries can be prepared in a variety of ways. For example, at block 90 random or targeted mutagenesis can be used to create a library of essential gene mutants. Random mutagenesis can be generated with error prone PCR, UV mutagenesis, chemical mutagenesis, mutator strains, or any other method that introduces any type of random mutation. Similarly, targeted mutagenesis is the complete or partial saturation mutagenesis of one or more particular amino acid residues, using any targeted mutagenesis strategy such as recombineering, Multiplex Automated Genome Engineering (MAGE), Enzymatic Inverse Polymerase Chain Reaction (EIPCR), Gene Splicing by Overlap Extension (SOEING) and the like. Specific approaches for the mutagenesis can also be found in Example 1. In one embodiment, the mutants have a series of mutations in the ORF of an essential gene, resulting in post-translational, ligand-dependent function of the essential gene product. In another embodiment, post-translational amino acid modifications conferring ligand-dependent function.

Essential gene mutant libraries can also be produced at block 80 with the use of a ligand-binding domain (LBD) that is inserted in or N or C-terminally fused to the essential gene product at block 100, where the ligand-binding domain is capable of controlling essential gene product function. Diversity is introduced into the linkers, the choice of insertion site and the choice of ligand-binding domain. The ligand-binding domain can either be a single entity such as an allosteric regulator or it can be a multimeric entity such as a 2-hybrid reconstitution in one embodiment.

This may also be accomplished at block 100 by translationally fusing a ligand binding domain to an essential gene. Examples of such ligand binding domains would be steroid hormone receptors (e.g. an estrogen receptor), sugar binding proteins (e.g. maltose binding protein), engineered allosteric domains (e.g. UniRapR, a permuted fusion of FKBP12 and FRB).

A library of linkers between the essential gene and the ligand binding domain are generally needed to effectively couple the ligand binding activity of the ligand binding domain to control over essential gene product function.

The essential gene library can be integrated directly into the genome by replacement of the WT copy of the target essential gene, or it can be transformed into the host cell along with a way of eliminating the activity of the genomic copy of the target essential gene (e.g. temperature sensitive mutant grown at restrictive temperature, CRISPR-Dcas9 mediated expression knockdown, cre-lox excision).

The library must be grown in the permissive condition (in the presence of the LBD's target ligand). If a selection is available and necessary (depending on library size), it can be used to reduce library size. Otherwise, individual mutants can be screened directly for ligand-dependent growth by replica plating (inspecting growth of individual mutants with complementing ligand and without complementing ligand).

A library of essential gene variants can also be generated at block 80 with ligand-dependent intein splicing to alter essential gene function at block 110. In one embodiment, diversity is introduced into linker junctions between the intein and the essential gene, the insertion site for the intein in the essential gene, or the intein sequence itself by using random or targeted mutagenesis. Inteins can be used as whole inteins, split inteins, or fusions with other domains (i.e. ligand binding domains).

For example, a wild type intein can be inserted into the open reading frame (ORF) of the essential gene. This insertion will not affect the phenotype of the organism, because the intein automatically splices itself out. However, in order to identify insertion sites, both the active and inactive forms of the intein must be inserted into candidate splicing sites of the essential gene. Insertion sites where the active intein allows growth and the inactive intein prevents growth (by abolishing essential gene function) can be used as insertions sites for ligand-dependent inteins that will result in synthetic auxotrophy. They can also be used to engineer ligand-dependent inteins de novo.

The constitutive splicing intein (harbored in the essential gene) is then prepared for mutagenesis by targeted mutagenesis, random mutagenesis or by ligand binding domain insertion. The resulting intein library is either integrated directly onto the organism's genome (replacing the WT copy of the essential gene) or if the essential gene intein library is on a plasmid, it is transformed into a strain in which the genomic copy of the relevant essential gene is a conditional mutant (i.e. temperature sensitive) and the transformants are grown at the restrictive temperature so that viability depends on the plasmid encoded phenotype. The resulting library of essential genes harboring mutant inteins are grown in the presence of a target complementing ligand to permit the growth of any ligand-dependent inteins present in the library.

If a selection is available, it can be used to reduce diversity of the library if needed. Screening is performed as previously described. In short, the growth of individual library members is assayed in the presence of complementing ligands or the absence of complementing ligands.

Once a robust ligand-dependent intein is generated, it is the ideal module for generating synthetic auxotrophy in any organism because of their context independence. A ligand-dependent intein generated in bacteria can be used to generate synthetic auxotrophs based on plants, animals, or fungi with very little modification other than inserting the ligand-dependent intein into the essential genes of those organisms or multiple essential genes for improved performance.

This is perhaps the easiest, quickest and least expensive way to make new live vaccines for emerging diseases. Acquire several isolates of the new pathogen, insert multiple ligand dependent inteins into multiple essential genes (if microbial) or all genes (if viral), and use the synthetic auxotrophic version of the pathogen to inoculate patients. Withholding the ligand prevents intein splicing and quickly eliminates the pathogens after an immune response has been developed).

Ligand-dependent inteins engineered to respond to diagnostic targets can be very easily inserted into enzymes that mediate colorimetric output to make chemical detection reagents (i.e. an intein that splices in the presence of 10 nM glucose can be inserted into an alkaline phosphatase enzyme to make colorimetric activity dependent on the presence of glucose).

The viability of an organism is contingent on the proper function of its essential genes. A mutant library on an essential gene will result in a set of organisms whose growth is tied to the function of the mutant essential gene.

The essential gene libraries that were prepared at block 80 of FIG. 2 are then subjected to selection and screening. Naïve essential gene libraries prepared at block 80 contain organisms of 3 basic phenotypes: viable mutant strains (functional essential genes), lethal mutant strains (non-functional essential genes), and ligand-dependent mutant strains (ligand-dependent essential genes). In order to isolate the desired ligand dependent strains, essential gene libraries are passed through a dual selection consisting of a positive selection based on chemically-complemented growth at block 120 and a negative selection at block 130. Survivors of the dual selection are enhanced with a second positive selection at block 140 and then screened for the desired phenotype at block 150.

The positive and/or negative selection steps are used (if available) to identify synthetic auxotrophs. The first positive selection 120 and optional second positive selection 140 steps are performed by growing a mutant library in conditions where growth/viability depends on the function of a mutagenized essential gene so the target ligand is present. The ability to grow at block 120 eliminates lethal mutants from the library because the lethal essential gene mutants fail to propagate. The viable essential gene mutants and the ligand-dependent essential gene mutants, complemented by target ligand, are able to propagate in the positive selection stage at block 120.

The organism can be forced to rely on the mutant essential gene at block 120 for growth/viability in various ways. For example, a plasmid-borne library of a mutagenized essential gene can be transformed into a cell harboring a temperature sensitive version of the relevant essential gene. Any other conditional mutant of the essential gene will also suffice, including transcriptional regulation, recombination, ligand-dependent, etc. . . . ). The transformants are then grown on the restrictive condition for the genomic mutant (i.e. high temperature) and the desired permissive condition for the ligand-dependent essential gene (i.e. the target small molecule that mediates complementation).

The negative selection at block 130 is performed to eliminate constitutively growing cells that do not require a ligand for growth. The negative selection at block 130 preferably grows the library of survivors in the absence of complementing ligand and in a condition in which growing cells are eliminated (i.e. conditions where growth-dependent lyses/death occurs). For example, this may include the addition of beta lactam antibiotics (i.e. penicillin technique) or some analogous negative selection system.

The positive and negative selections at block 120 and 130 can cycled as needed to identify and enrich desirable phenotypes. A screen is used at block 150 to identify synthetic auxotrophs.

The method of FIG. 2 can be adapted to different positive and negative selection schemes. This can be illustrated in the FIG. 3 and FIG. 4. The embodiment 160 shown schematically in FIG. 3 uses a negative selection growth-based mechanism of action that selectively kills actively dividing cells based on beta lactam antibiotics (i.e. penicillin). The naïve essential gene libraries 170 that were prepared contain organisms of viable mutant strains with functional essential genes (open), lethal mutant strains with non-functional essential genes (black), and ligand-dependent mutant strains with ligand-dependent essential genes (shaded). In the first positive selection 180, the target ligand is present in the growth media.

Lethal mutants (black) fail to propagate due to a non-functional essential gene or because a molecule that might have mediated complementation was not included in the target ligand pool.

The two types of survivors 190 are then exposed to a negative selection 200 in the absence of the target ligand and in the presence of penicillin that selectively kills actively dividing cells. In the absence of complementing target ligands, the ligand-dependent strains do not grow and are unharmed by the presence of the penicillin. Viable mutants that can grow in the restrictive conditions 200 are killed by penicillin's antibiotic activity.

An optional second positive selection 220 is performed. The survivors 210 of the negative selection 200 are transferred to a non-restrictive growth conditions that contain the complementing target ligands to enhance the number of organisms. The synthetic auxotrophs 230 are then screened.

In the alternative embodiment 240 shown schematically in FIG. 4, the naïve essential gene libraries 250 that were prepared contain dapD KO organisms of viable mutant strains with functional essential genes (open), lethal mutant strains with non-functional essential genes (black), and synthetic auxotroph strains with ligand-dependent essential genes (shaded). In this illustration, DAP rescues the DAP KO organisms.

This initial library is grown in the presence of a complementing ligand and DAP in the positive selection 260. The lethal mutants are eliminated and the survivors 270 of viable mutants and synthetic auxotrophs are collected. The survivors 270 are then exposed to negative selection 280 conditions that does not contain the target ligand or DAP. In the restrictive growth conditions of the negative selection 280, growth without DAP results in the lyses of growing cells that lack the dapD gene eliminating the viable mutants. The ligand-dependent synthetic auxotrophs do not grow in the absence of the complementing ligands.

Survivors 290 of the negative selection 280 can optionally be enhanced with a second positive selection 300 with positive growing conditions and the survivors 310 are then collected and screened. The positive and negative selections can also be repeated.

The screened ligand-dependent synthetic auxotrophs can be designed for and incorporated into a number of different applications. For example, the collected strains can be used as a metabolic engineering tool where the synthetic auxotrophs are developed to respond to a target small molecule. In one embodiment, the tool can utilize a live-die selection strain to identify novel enzyme variants producing the target ligand (i.e. that complements the synthetic auxotroph) from large enzyme libraries.

Likewise, the methods can produce a selection strain that optimizes production of a given metabolic pathway for the target small molecule.

In another embodiment, the methods can be used to provide a protein switch engineering tool where essential genes that are controlled by ligand-binding domains that are engineered to respond to a target small molecule and the engineered ligand-binding domains are fused to other proteins to impose small molecule control in order to create novel transcription factors, feedback circuits in engineered metabolic pathways or in vitro diagnostic reagents.

Perhaps the most significant use of the synthetic auxotrophs with ligand-dependent essential genes is as a biosafety strategy and technology. For example, the synthetic auxotroph organism can be eliminated by withholding the complementing ligand.

The growth, viability, and function of the ligand-dependent synthetic auxotroph can be restricted to a time and space in which a complementing ligand is supplied. This control can be used as a biosafety strategy to improve control and containment over engineered organisms/biological systems intended for any use, as in therapeutic organisms/biological systems, such as engineered immune cells, oncolytic viruses, phage therapies, engineered probiotics (i.e. gut commensals), gene therapies, live vaccines and gene delivery vectors.

Figure 5:
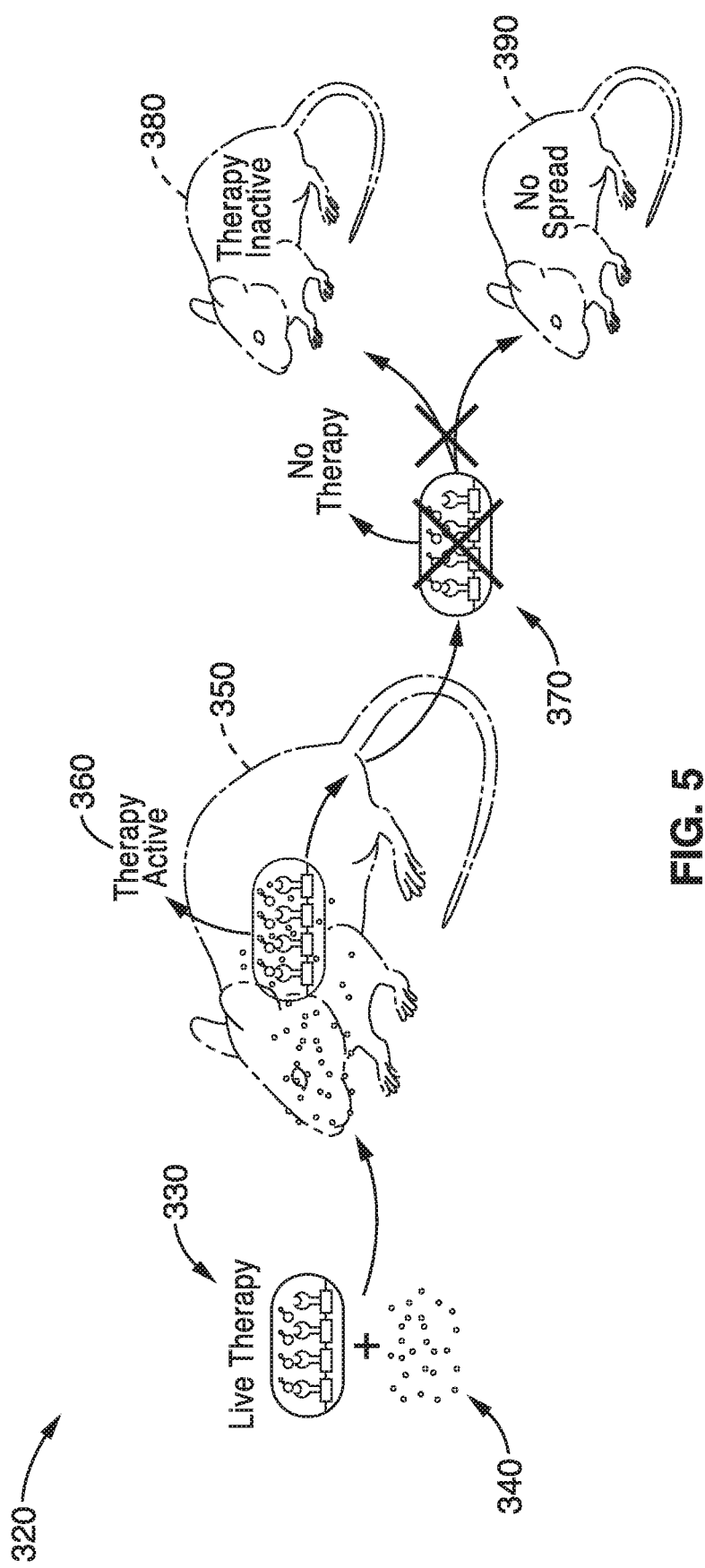
FIG. 5 is a schematic illustration of a biosafety application of the technology in an animal context.

For example, therapeutics with ligand-dependent essential genes can be formulated that can be contained in the treatment or research system as shown in FIG. 5. The system 320 illustrated in FIG. 5 provides a live therapeutic 330 with a ligand-dependent essential gene.

The live therapeutic 330 and activating ligand 340 are fed to the subject mouse 350. The therapy 360 is active and the live therapeutic performs in the mouse only if the activating ligand 340 is supplied to the subject. The concentration of the activating ligand 340 that is established in the subject 350 may equal control over the therapeutic organism 330 potency.

The methods can also be adapted for used in agricultural organisms and biological systems, such as live pesticides (biocides), crop/livestock microbiome products, engineered plants or animals, crop/livestock gene delivery vectors as well as with industrial organisms and biological systems, such as the biological production of chemicals, bioremediation and engineered fermentations.

Removal of the activating ligand from the results in the termination of activity of the therapeutic 370 or results in the death of the therapeutic 370. Live therapeutic that is inside or outside a mouse 380 without the activating ligand will result in the termination of activity or death of the therapeutic organism 370. Dead or inactive therapeutic organisms mean that there is no production of any therapeutic activity or proliferation of the organism inside the mouse 390.

The technology of this disclosure may be better understood with reference to the accompanying examples, which are intended for purposes of illustration only and should not be construed as in any sense limiting the scope of the present technology as defined in the claims appended hereto.

Example 1

In order to prove the concept of the synthetic auxotrophs and the engineering methods, a biosafety strain of BL21 (DE3) of *E. coli* was produced using the methods of the present technology as outlined in FIG. 2 and tested. Synthetic auxotrophs based on a ligand-dependent essential gene using 5 essential genes as test cases: pheS, dnaN, tyrS, metG, and adk were produced.

To identify ligand-dependent strains, a candidate list of essential genes necessary for *E. coli*'s viability was assembled. The list was narrowed to those with a solved crystal structure so that the residues for mutagenesis could be chosen. Mutations were targeted to regions near the surface, but still within the hydrophobic core. Portions of the crystal structure containing groups of large, hydrophobic residues (for example Trp, Phe, Met, Ile, Leu) were subjected to targeted mutagenesis in 3 different ways, as follows.

In the first approach (on pheS and dnaN), mutagenesis was targeted such that a central large hydrophobic residue was mutated to glycine while surrounding residues were randomized using the degenerate codon NNK. Initially, these libraries were plasmid-based and were transformed into pheS$^{ts}$ or dnaN$^{ts}$ temperature sensitive strains at the permissive temperature. For selections, screens, and phenotypic analysis, the libraries were grown at the restrictive temperature. This procedure would abolish function of the conditional genomic essential gene in question and reveal the phenotype encoded by the plasmid-borne library member. Thereafter, libraries were generated directly on the genomic copy of the targeted essential gene. This reduced experimental complexity and allowed the engineering of the essential genes lacking temperature sensitive mutants.

In the second approach applied on tyrS and metG, libraries were generated on the genome and targeted to similar hydrophobic domains, but mutagenesis was confined in primary sequence to fit within a 7 amino acid residue window. This allowed a single 60-bp recombineering oligo to contain genome-targeting homology regions and mutagenic NNK codons. The preferred target for mutagenesis was a β strand passing through a hydrophobic core. In such β strands, every other amino acid will generally point in the same direction within the protein's secondary structure. These β strands were targeted by randomizing a set of 4 amino acids on 1 or both sides of a β sheet.

For example, genome libraries designed by randomizing strips of neighboring amino acids were integrated directly into the genome by recombineering. A degenerate library oligo was used to introduce mutations into the genome. A CRISPR-Cas9-mediated double strand break targeted to wildtype DNA sequences was used to enrich for organisms mutagenized at the desired locus. Upon transformation, the resulting library of strains was then subjected to selections and screens.

Libraries were encoded on 60-bp recombineering oligos (library oligos). Library oligos (478_GLU45.1 for metG libraries and 475_LEU36.1 for tyrS libraries) contained a 5' homology region of 21-bp, a 21-bp window for degeneracies, and an 18-bp 3' homology arm. Library oligos were accompanied by a helper plasmid (bgg472), encoding a sgRNA targeted to the wildtype sequence to which the library oligo was homologous. The library oligo and its partner sgRNA plasmid were co-transformed into freshly prepared, electrocompetent MC1061 cells harboring pSIM5 encoding the lambda-red genes and DS-SPcas encoding Cas9. Cells were recovered for 1 hour in 2YT and then spread on LB agar plates containing the ligand or pool of interest and antibiotics selecting for DS-SPcas (spectinomycin 50 µg/ml final concentration) and the sgRNA plasmid (kanamycin 50 µg/ml final concentration). During this incubation, the addition of complementing chemical was found to be optional.

The third approach (on adk) was similar to the second approach, with the additional design parameter of constraining mutagenesis to within 60 bp of the 5' end of the essential gene to be engineered. This simplified library fabrication, because a single PCR (using a selectable marker template) could generate a genomic integration fragment. The integration cassette consisted of an antibiotic marker, a recoded 5' sequence of the targeted gene (to prevent premature crossover), and amino acid degeneracies. In addition to the three targeted mutagenesis methodologies, random mutagenesis was also explored as a means of improving weak, initial ligand-dependent phenotypes. Error prone PCR was used to generate libraries on ligand-dependent alleles that entered directed evolution experiments.

In one illustration, the genome library was fabricated with Lambda-Red recombination. To replace wildtype alleles with corresponding 5' mutant alleles from a mutant library, an integration product was generated. The integration product consisted of (from 5' to 3') of a 5' genomic-targeting homology region, a selectable marker driven by a constitutive promoter, a canonical RBS, recoded DNA of the essential gene (to prevent premature crossover-mediated library excision), the desired degeneracies, and finally a 3' genomic-targeting homology region (see bgg524 for knock-in fragment). This PCR fragment was transformed into freshly prepared electrocompetent MC1061 cells harboring pSIM5. Cells were recovered for 1 hour in 2YT (as before, the addition of complementing chemical was found to be optional) and then plated on LB agar plates containing the chemical (or chemicals) of interest and spectinomycin to select for the antibiotic marker of the library integration PCR fragment.

The resulting library was then subjected to selection and screening. This method was used to knock-in error prone PCR libraries with the exception that there was no recoding of the ORF and the entirety of the ORF was included on the knock-in fragment. Error prone PCR libraries were generated with the GeneMorph II Random Mutagenesis Kit (Agilent) according to manufacturer's recommendations.

Protein engineering was necessary but not sufficient for generating a ligand-dependent strain. A complementing molecule must also be identified. A library approach was used to allow the inspection of a larger search space of ligand candidate solutions. A pool of chemicals was used to increase the odds of finding ligand-dependent strains. This was done for two reasons. First, it was not known beforehand which chemicals might mediate chemical complementation. Second, the possibility that there might be multiple molecules capable of chemical complementation and that a library approach allows the identification of strains responding to different ligands. The choice of potential complementing chemicals was based on 3 practical criteria: low-cost, low-risk (non-explosive, non-flammable, and non-carcinogenic), and media-soluble.

Out of the ~300 essential genes in *E. coli*, 8 essential genes were targeted for mutagenesis with 10 libraries total. From this, 5 essential genes yielded ligand-dependent strains of which 1 mutant each was characterized. It was concluded that ligand-dependent phenotypes are not rare and can be readily generated using classical microbial genetics techniques.

Example 2

To further demonstrate the methods outlined in FIG. 2 and FIG. 3 the essential gene libraries that were prepared were subjected to selection and screening. Naïve essential gene libraries prepared at block 80 contain organisms of 3 basic phenotypes: viable mutant strains (functional essential genes), lethal mutant strains (non-functional essential genes), and ligand-dependent mutant strains (ligand-dependent essential genes). In order to isolate the desired ligand dependent strains, essential gene libraries were passed through a dual selection consisting of a positive selection based on chemically-complemented growth and a negative selection based on a penicillin technique. Survivors of the dual selection were screened for the desired phenotype.

For the positive selection 120, a library of strains resulting from a mutagenized essential gene was grown in the presence of 4 chemicals. Positive selections were based on viability in the permissive condition. Permissive conditions consisted either of 1M benzothiazole in DMSO used at 1000× (to generate pheS.GL2) or a mixture of small molecules (chemical pool) consisting of 50 mM benzothiazole, 50 mM indole-3-butyric acid, 25 mM indole, and 25 mM 2-aminobenzothiazole dissolved in DMSO as 100× (to generate all other SLiDE strains). Pooling these ligands increased the efficiency of the engineering process, so that a single positive selection could be run for multiple chemicals.

In the permissive condition of those in the four chemical pool, the three basic phenotypes of an essential gene library could be selected based on their capacity for growth. Lethal mutants failed to grow due to a broken essential gene or because a molecule that might have mediated complementation was not in included in the chemical pool. Viable mutants grew regardless of the presence of chemicals. The ligand-dependent strains grew in the permissive condition because they were chemically complemented by at least one of the molecules in the chemical pool at block 120 of FIG. 2. Because lethal mutants were not viable, the phenotypic composition of the essential gene library was reduced from 3 to 2: viable strains and ligand-dependent strains. Library members surviving the positive selection were subjected to a negative selection at block 130 of FIG. 2.

The negative selection at block 130 in this illustration was based on the penicillin technique. The technique relies on penicillin's growth-based mechanism of action that selectively kills actively dividing cells. This method is used as a negative selection to eliminate viable mutants. In the adaptation of the penicillin technique, library members that survived the positive selection at 120 were transferred to a restrictive growth condition that did not contain complementing chemicals.

Briefly, libraries were re-suspended in media, washed once to remove any complementing chemicals, and re-inoculated into 100 ml of plain 2YT containing no complementing chemicals (the restrictive condition) at an OD600 of 1-5. Cells were grown at 37° C. with aeration for 1-2 hours in order to account for phenotypic lag. Penicillin was added at a final concentration of 1 mg/ml. The cells were grown for between 5-48 hours. Cells were harvested by centrifugation, washed twice, and spread on large LB agar plates containing the desired complementing chemicals for screening.

In the absence of complementing ligands, the ligand-dependent strains did not grow and were unharmed by the penicillin. Viable mutant library members that grew in the restrictive condition were killed by penicillin's antibiotic activity.

A second positive selection at block 140 was performed in order to enrich for desirable ligand-dependent strains. Library members surviving the negative selection were collected, residual penicillin was washed away, and cells were spread onto LB agar plates containing complementing chemicals. Resulting colonies were screened at block 150 for ligand-dependent growth by replica-spotting onto LB agar plates with and without complementing chemicals. Strains that grew only in the presence of chemicals were chosen for further characterization.

In this example, the ligand-dependent strains were generated for 5 essential genes (pheS, dnaN, tyrS, metG, and adk). Each ligand-dependent strain carried between 3 and 7 mutations at the targeted essential gene (Table 1). A mixture of 4 small molecules was used to generate the ligand-dependent strains. Each resulting strain was tested against each small molecule individually. The most promiscuous strain, metG.GL15, was complemented by all 4 ligands. Other mutants responded to 2 or 3 ligands. Additionally, escape frequency was measured on media lacking any of the 4 ligands. The highest escape frequency was $8\times10^{-4}$ for adk.GL1, while the lowest escape frequency was $3\times10^{-9}$ for pheS.GL2.

The ligand-dependent strain pheS.GL2 was derived from a directed evolution procedure using both targeted and random mutagenesis. The ligand-dependent strain pheS.GL2 failed to grow in on LB agar plates containing no ligand, with an escape frequency of $3\times10^{-9}$. The ligand-dependent strain pheS.GL2 was strongly complemented by 1 mM benzothiazole and 0.5 mM indole. Despite undergoing 2 rounds of error-prone PCR, all of the mutations in pheS.GL2 were contained within a single stretch of approximately 15 Angstroms according the crystal structure of the wildtype protein (PDB 3PC0). All mutations were located between 15-25 Angstroms from the AMP substrate in the active site.

Sequence analysis of pheS.GL2 escape mutants suggested second-site suppressor mutations as the primary mode of escape. Out of the six escape mutants that were sequenced, 5 mutants contained Q169H, (an active site residue, approximately 10 Angstroms away from the substrate) and 1 mutant contained T162N (a near-active site residue, approximately 20 Angstroms away from the AMP substrate) (Table 2).

The ligand-dependent strain tyrS.GL7 and metG.GL15 were generated in under 2 weeks with a single cycle of protein engineering. This consisted of randomizing 4 hydrophobic core amino acids, dual selection, and screening. Ligand-dependent strain tyrS.GL7 showed comparable escape frequency to pheS.GL2. This mutant exhibited dose-dependent growth between 250-1000 µM Benzothiazole and was also complemented by indole. Inspection of the wild-type crystal structure of tyrS and metG show close proximity between mutations and enzyme substrate (4-10 Angstroms for tyrS.GL7 and 7-20 Angstroms for metG.GL15). The simplified library design approach can readily yield ligand-dependent strains and four mutations was shown to be sufficient for generating suitable ligand-dependent strains.

To characterize the specificity of the produced ligand-dependent strains towards ligands, all strains were examined for complementation by a panel of 30 additional ligands. Only 2 ligands (Indole-3-acetic acid and L-histidine methyl ester) were found to complement metG.GL15. The remaining 28 ligands produced no growth in the other isolated ligand-dependent strains.

Example 3

To demonstrate the utility of the ligand-dependent phenotypes for containment of genetically engineered organisms, two and then three ligand dependent (SLiDE alleles) were combined into BL21(DE3) bacteria. Multiple ligand-dependent alleles should reduce the escape frequency due to suppressor mutations. In addition, combining several of these modifications into a single strain should also decrease escape through horizontal gene transfer.

The combination of 2 SLiDE alleles into the industrially relevant strain BL21(DE3) of $E.\ coli$ created a biosafety strain with an escape frequency of $5\times10^{-10}$ and a combination of 3 SLiDE alleles in BL21(DE3) resulted in an escape frequency below the limit of detection of $3\times10^{-11}$.

In particular, previously identified ligand-dependent strains were used as donor cells to generate P1 phage lysate for transduction. Alternatively, identified mutations were re-integrated into a new host using Cas9-recombineering methodology. BL21(DE3) was first transformed with PKD46-cas9(25) and then transformed with a mutagenic oligo encoding the tyrS.GL7 mutation as well as a helper plasmid expressing a sgRNA (bgg539) targeting the wild-type sequence in the genome. After clearing the helper plasmid, the resulting strain was P1-transduced with a ΔtnaA:FRT-kanR-FRT cassette in order to knockout tnaA.

This strain was subsequently transduced with a P1 lysate containing FRT-DHFR-FRT upstream of metG.GL15. The resulting strain was transformed with pFLP2 (in order to remove antibiotic markers associated with metG.GL15 and ΔtnaA), outgrown in carbenicillin (100 µg/ml final concentration) for 4 hours, then spread on LB agar plates containing 1 mM benzothiazole and no antibiotic. Viable colonies were screened for antibiotic marker clearance and sequence confirmed at the relevant loci. This strain was used as the double ligand-dependent strain.

Subsequently, the double ligand-dependent strain was P1-transduced with kanR-tagged-pheS.GL2. Resulting colonies were sequenced in order to confirm that they harbored all 3 ligand-dependent mutations. These cells were used as triple ligand-dependent strains.

Escape frequency was determined by spotting a serial dilution (of log 10 increments) of the strain of interest onto LB agar plates of the restrictive condition (consisting of no ligand) and the permissive condition (benzothiazole). Plates containing DMSO were also spotted to ensure no complementation by the solvent. The escape frequencies of the ligand-dependent strains were continuously monitored during the protein engineering process. The escape frequency of the obtained ligand-dependent strains were assayed on two or three separate occasions, using four biological replicates derived from re-suspended colonies. Escape frequency was calculated by dividing the surviving CFU on the restrictive condition by the surviving CFU on 1 mM benzothiazole. The log escape frequencies were used to calculate a mean and standard deviation.

For the double and triple ligand-dependent strains, an overnight culture was inoculated into 3 ml 2YT containing 1 mM benzothiazole. The cultures were grown in 24 well blocks at 30° C. with 750 rpm orbital velocity. The next morning, cultures were washed 3 times with 10% glycerol and re-suspended in 1.5 ml 10% glycerol. From this, 1 ml was spread onto a 220 mm LB agar screening plate containing no complementing benzothiazole. Then 10 µl from each 10-fold serial dilution spanning 8 orders of magnitude was spotted onto a permissive plate in order to titer CFU plated on the restrictive condition. All plates were grown overnight at 37° C. The strain escape frequencies of double and triple ligand-dependent strains were calculated by dividing any escape mutants (colonies forming on the restrictive condition) by the total CFU plated as calculated from the serial dilution spotted onto the permissive condition.

In this illustration, two ligand dependent alleles, tyrS.GL7 (escape frequency $7\times10^{-8}$) and metG.GL15 (escape frequency $3\times10^{-4}$) were combined to produce a double ligand-dependent strain with an escape frequency of $5\times10^{-10}$, exceeding the biosafety threshold of 1 escape mutant per $1\times10^{8}$ cells. The escape frequency was observed to steadily increase over the first 4 days, increasing nearly 1000-fold to $4\times10^{-7}$. From day 4 to day 10, the escape frequency increased 10-fold to $1\times10^{-6}$. The double ligand-dependent strain displayed dose-dependent growth in microplate-based growth curve experiments.

In order to further reduce escape frequency, pheS.GL2 was transferred by P1 transduction into the double ligand-dependent strain to generate a triple ligand-dependent strain. The triple ligand-dependent strain escape frequency dropped below the limit of detection of $3\times10^{-11}$ on days 1 and 2. As with the double mutant, the escape frequency increased over the duration of the experiment, stabilizing at $2\times10^{-7}$ after 10 days. The triple ligand-dependent strain also displayed dose-dependent growth in liquid culture.

Example 4

To illustrate an alternative embodiment of ligand-dependent function of an essential gene product formation, a ligand-binding domain was inserted and fused in an essential gene product where the ligand-binding domain is capable of controlling essential gene product function. In this illustration, a ligand-controlled protein conformational switch called uniRapR was selected and inserted.

The uniRapR switch is a fusion of fkbp12 and FRB protein domains that heterodimerize around the ligand rapamycin. In the absence of rapamycin, uniRapR is unstable (higher heat capacity, higher rmsd values, higher distance between C-alpha atoms as a function of temperature, and different position of subdomains relative to ligand).

In the presence of rapamycin, uniRapR is much more stable (e.g. lower heat capacity, lower rmsd values, lower distance between C-alpha atoms as a function of temperature, and far different position of subdomains relative to ligand). The uniRapR switch domain can be used to control proteins.

The uniRapR was inserted into an essential gene as a means to create ligand-dependent essential genes in this case. The uniRapR switch was selected because it had a suitable structure to make the insertion of the domain into the target gene easy. Other selections included an estrogen receptor and a maltose binding protein.

In this illustration the uniRapR switch was inserted into the essential gene dnaN. The dnaN molecule is a homodimer that forms a ring or "clamp" around DNA that allows all the DNA processing enzymes to have much higher processivity. This was selected because there are a several loops that would make good insertion sites for uniRapR and four insertion sites were selected.

Starting with a plasmid borne copy of wild type dnaN under constitutive expression, the uniRapR domain was inserted into 4 candidate insertion sites with a 3 amino acid linker library upstream and downstream of the uniRapR domain. The resulting libraries (all four insertion sites with their linker libraries) were pooled and transformed into a strain of E. coli with a mutation on the genomic copy of dnaN that made the protein temperature sensitive (dnaN protein from genome is non-functional at 42° C. and it is bactericidal lethal).

The transformants were grown at 42° C. (lethal temperature for genomic copy so as to force bacteria to rely on the plasmid copies with the uniRapR insertions) as well as with the addition of 10 uM rapamycin (to complement the function of any rapamycin-dependent insertional fusion dnaN mutants) and allowed to grow overnight.

The next day, the survivors were collected and remaining rapamycin was removed with a series of centrifugation and resuspension with PBS cycles. Once the remaining rapamycin was removed, the mutant library was used to inoculate a flask containing 2YT media (100 ml) to approximately OD=1. The culture was then grown with shaking at 42° C., the restrictive temperature, for 1 hour. Growth in the absence of rapamycin and at 42° C. was meant to kill any rapamycin-dependent mutants (the desired strains) in order to stop their growth (before the addition of penicillin G salt).

The Penicillin G salt was added to the flask after at least 1 hour. Strains continuing to grow at 42° C. without rapamycin were lysed, while any desired mutants had already died (dnaN mutants are bactericidal) and remained intact.

A negative selection was then performed for approximately 7 hours, after which the culture was centrifuged and the lysed cell debris and dead (but intact cells) were collected. 3 cycles of resuspension with PBS and centrifugation were used to leach away any plasmid DNA from the lysed cells that harbored non-ligand-dependent dnaN mutants. The remaining material was then mini-prepped in order to extract plasmid DNA from dead, but intact cells.

The extracted plasmid DNA was re-transformed into fresh dnaN-temperature sensitive strains and grown on LB agar supplemented with rapamycin at 42° C. The next day colonies were picked and re-spotted onto LB agar plates with or without rapamycin and grown at 42° C. The third day, a mutant was identified that displayed rapamycin-dependent growth. The biological replicates of a 10-fold serial dilution of the rapamycin-dependent mutant grown without rapamycin (clear columns) or with 2.5 micromolar rapamycin (columns with growth) were prepared. All growth took place at 42° C.

The phenotype was verified and it displayed dose-dependent rapamycin growth at 42° C. with highest activity between 1-10 uM of rapamycin. It had an escape frequency of approximately 1E-5 (this is actually the limit of detection and the performance is probably better). The mutant was also grown on plates with indole and benzothiazole instead of rapamycin to test for nonspecific chemical complementation and no growth was detected without the proper ligand.

Thereafter, the ligand-dependent switch DNA was isolated and sequenced. It was found to contain a uniRapR insertion at position 185 of dnaN (replacing the GLY185).

Example 5

To illustrate an alternative embodiment of ligand-dependent function of an essential gene product formation, a ligand-dependent intein was inserted into an essential gene such that the unspliced fusion protein is inactive, but a functional protein is produced upon ligand-mediated intein splicing.

A split intein called GP41 was selected and obtained. The GP41intein was then significantly modified by fusing two intein halves with a GSGSGSGSGS linker. An iFKBP domain was inserted in the middle of that GS linker as a possible ligand-binding domain option for downstream engineering. A wild type (WT) intein without the iFKBP insertion was also prepared.

A mutant version of the GP41 intein was also generated in which the catalytic residues at the C terminal, His, Asn, Ser, all of which are essential for intein function, were mutated to Gly.

Both the WT intein and the Gly-Gly-Gly mutant were inserted into various positions in pheS and dnaN, replacing Serine residues. The WT GP41 intein leaves behind the C-terminal Serine, so the resulting spliced protein is indistinguishable from a WT version.

Screening for insertion sites where the functional intein permitted growth with the pheS and dnaN insertions was conducted. The triple Gly mutant version resulted in death. This was observed because a non-splicing intein in the middle of an essential gene would dramatically disrupt the structure and function.

An insertion site in pheS and dnaN was found where the functional intein resulted in viable cells because the essential gene was functional due to proper intein splicing, but in which the triple Gly mutant resulted in death. Inteins appeared to splice well at 37° C. and 42° C.

The next step was to engineer ligand-dependent intein function. This was accomplished by using a plasmid encoding a dnaN with the GP41 (not split as in the WT) fused with an iFKBP domain translationally inserted into dnaN at an insertion site found to eliminate dnaN function in the absence of splicing. Because this variant spliced well, this dnaN-intein plasmid was able to complement the gene function of a temperature sensitive genomic copy of dnaN mutant when grown at the restrictive condition of 42° C.

A variety of saturation mutagenesis libraries targeting a combination of surface exposed and semi-buried residues on the intein structure were then designed, ignoring the iFKBP domain as well as the dnaN sequence. The resulting plasmid library was then transformed into dnaN-temperature sensitive strains (dnaN-temp sensitive on the genome). The resulting transformants were grown on LB agar plates containing 5 chemicals: rapamycin, saccharin, acetaminophen, raspberry ketone, and benzothiazole. These chemicals were chosen based on being either useful commercially or likely to result in the desired phenotype. As before the library was grown at 42° C. so that the strains would have to rely on the plasmid borne mutagenized copies of the dnaN-intein-iFKBP fusion proteins.

The next day the libraries were scraped, and transferred to fresh media for a penicillin technique counter selection performed exactly as described before with FIG. 2 and FIG. 3. After the negative selection, intact cells were mini-prepped and the DNA was re-transformed into fresh cells and the transformants were grown on the same chemicals as indicated above at 42° C.

The next day, colonies were picked, serially diluted tenfold and spotted onto plain LB agar plates and LB agar plates containing a pool of candidate complementing ligands and grown at 42° C. (to uncover phenotype of plasmid born copy of dnaN).

On the third day, the phenotypes were inspected and grown in the presence of complementing ligands were found to provide a growth advantage. Colonies grown with benzothiazole were found to be approximately 2-5 times larger (by eye). Ten isolated mutants were sequenced and from this, 4 mutant sequences were identified. All mutants had a LYS79LEU in the intein (with respect to intein AA sequence).

The original 4 hits that were identified were mutagenized with error prone PCR and another round of saturation mutagenesis targeting the C terminal intein domain, near the active site. The same library fabrication, selection, and screening methodologies were then used as with the other examples of ligand-dependent mutants.

From the description herein, it will be appreciated that the present disclosure encompasses multiple embodiments which include, but are not limited to, the following:

1. A method for engineering a synthetic auxotroph based on a ligand-dependent essential gene function, the method comprising: (a) identifying one or more essential genes and essential gene products in an organism; (b) selecting one or more ligands; (c) modifying at least one essential gene to produce ligand-dependent function in an essential gene product; and (d) negatively selecting for organisms with one or more mutated ligand-dependent essential genes; (e) wherein essential gene function does not occur in the absence of the ligand.

2. The method of any preceding embodiment, further comprising: positively selecting surviving organisms of the negative selection to enhance the number of surviving organisms that have ligand-dependent essential genes.

3. The method of any preceding embodiment, further comprising: positively selecting for organisms with one or more mutated ligand-dependent essential genes using chemical complementation; and negatively selecting for organisms with one or more mutated ligand-dependent essential genes using an antibiotic.

4. The method of any preceding embodiment, wherein the modification of an essential gene is performed by random mutagenesis of the open reading frame of an essential gene with a process selected from the group consisting of error prone PCR, UV mutagenesis, chemical mutagenesis and mutator strains.

5. The method of any preceding embodiment, wherein the modification of an essential gene is performed by targeted mutagenesis of the open reading frame of an essential gene for one or more amino acids with a process selected from the group of recombineering, Multiplex Automated Genome Engineering (MAGE), Enzymatic Inverse Polymerase Charin Reaction (EIPCR) and Gene Splicing by Overlap Extension (SOEING).

6. The method of any preceding embodiment, wherein the modification of an essential gene is an N or C terminal fusion of a ligand-binding domain that confers ligand-dependent function to the essential gene product.

7. The method of any preceding embodiment, wherein the modification of an essential gene is a ligand-dependent intein domain that confers ligand-dependent splicing in order to functionalize the essential gene.

8. The method of any preceding embodiment, further comprising: modifying a second essential gene to produce ligand-dependent function in a second essential gene product in response to a second ligand.

9. The method of any preceding embodiment, wherein the two ligand-dependent essential genes are genes selected from the group of structural genes, regulatory genes and signaling genes.

10. A method for engineering a synthetic auxotroph based on a ligand-dependent essential gene function, the method comprising: (a) identifying one or more essential genes and essential gene products in an organism; (b) preparing a library of essential gene mutants; (c) selecting one or more ligands; (d) performing a positive selection on the library of essential gene mutants in the presence of a selected ligands and positive growth conditions; (e) performing a negative selection on the library of essential gene mutants in the absence of the selected ligand in negative growth conditions; and (f) collecting survivors of the negative selection; (g) wherein the negative growth conditions of the negative selection eliminates growing organisms.

11. The method of any preceding embodiment, further comprising: performing a positive selection of collected survivors of the negative selection to enhance the number of surviving organisms that have ligand-dependent essential genes; and screening organisms for desired phenotypes.

12. The method of any preceding embodiment, wherein the library of essential gene mutants is generated using random mutagenesis of the open reading frame of an essential gene with a process selected from the group consisting of error prone PCR, UV mutagenesis, chemical mutagenesis and mutator strains.

13. The method of any preceding embodiment, wherein the library of essential gene mutants is generated using targeted mutagenesis of the open reading frame of an essential gene for one or more amino acids with a process selected from the group of recombineering, Multiplex Automated Genome Engineering (MAGE), Enzymatic Inverse Polymerase Charin Reaction (EIPCR) and Gene Splicing by Overlap Extension (SOEING).

14. The method of any preceding embodiment, wherein the library of essential gene mutants is generated using N or C terminal fusion of a ligand-binding domain that confers ligand-dependent function to the essential gene product.

15. The method of any preceding embodiment, wherein the fused ligand-binding domain further comprises a linker.

16. The method of any preceding embodiment, wherein the fused ligand-binding domain is selected from the group of a hormone receptor, a sugar binding protein and an allosteric regulator.

17. The method of any preceding embodiment, wherein the fused ligand-binding domain is a 2-hybrid reconstitution multimeric entity.

18. The method of any preceding embodiment, wherein the library of essential gene mutants is generated using insertional fusion of a ligand-binding domain that confers ligand-dependent function to the essential gene product.

19. The method of any preceding embodiment, wherein the library of essential gene mutants is generated using insertional fusion of a ligand-dependent intein domain that confers ligand-dependent splicing in order to functionalize the essential gene.

20. The method of any preceding embodiment, wherein the negative selection comprises an antibiotic.

21. A synthetic auxotroph, comprising: (a) an organism, with one or more mutated ligand-dependent essential genes, the one or more mutated ligand-dependent essential genes producing one or more genetically induced phenotypes; (b) wherein the presence of one or more specific ligands reverses the one or more genetically induced phenotypes.

22. The synthetic auxotroph of any preceding embodiment, wherein the synthetic auxotroph organism is an organism selected from the group of single celled eukaryotes, multicellular eukaryotes, commensal organisms and viruses.

23. The synthetic auxotroph of any preceding embodiment, wherein the synthetic auxotroph organism is a bacteria selected from the group of bacteria consisting of actinobacteria, bacteroidetes, cyanobacteria, firmicutes and proteobacteria.

24. The synthetic auxotroph of any preceding embodiment, wherein the organism comprises *E. coli* strain BL21 (DE3).

25. The synthetic auxotroph of any preceding embodiment, wherein the organism comprises a biosafety strain with an escape frequency of less than approximately $3\times10^{-11}$.

26. The synthetic auxotroph of any preceding embodiment, wherein the mutation comprises an N or C terminal fusion of a ligand-binding domain that confers ligand-dependent function to an essential gene product.

27. The synthetic auxotroph of any preceding embodiment, wherein the mutation comprises a ligand-dependent intein domain that confers ligand-dependent splicing in order to functionalize the essential gene.

28. The synthetic auxotroph of any preceding embodiment, wherein the ligand-dependent essential genes are genes selected from the group of structural genes, regulatory genes and signaling genes.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

List of Mutations for Selected Ligand-Dependent Strains. Italicized residues were mutagenized but remained wild type.

| Mutant | Mutations | | | | | | |
| --- | --- | --- | --- | --- | --- | --- | --- |
| dnaN.GL7 | H191N | R240C | I317S | F319V | L340T | V347I | S345C |
| pheS.GL2 | F125G | P183T | P184A | R186A | I188L | | |
| tyrS.GL7 | L36V | C38A | F40G | P42P | | | |
| metG.GL15 | E45Q | N47R | I49G | A51C | | | |
| adk.GL1 | I3I | I4L | L5I | L6G | | | |

TABLE 2

Mutations in 6 pheS.GL2 Escape Mutants

| Revertant | Mutations |
| --- | --- |
| pheS.GL2R1 | T162N |
| pheS.GL2R2 | Q169H |
| pheS.GL2R3 | Q169H |
| pheS.GL2R4 | Q169H |
| pheS.GL2R5 | Q169H S95F |
| pheS.GL2R6 | Q169H S95F T183P |

What is claimed is:

1. A synthetic auxotroph, comprising:
(a) an organism, with one or more mutated essential genes, said one or more mutated essential genes are ligand-dependent essential genes encoding post-translational ligand-dependent essential gene products producing one or more genetically induced ligand-dependent phenotypes;
(b) wherein the presence of one or more specific ligands reverses said one or more genetically induced phenotypes through ligand-dependent, post-translational modulation and control of mutated essential gene product function.

2. The synthetic auxotroph of claim 1, wherein the organism is an organism selected from the group of single celled eukaryotes, multicellular eukaryotes, commensal organisms and viruses.

3. The synthetic auxotroph of claim 1, wherein the organism is a bacteria selected from the group of bacteria consisting of actinobacteria, bacteroidetes, cyanobacteria, firmicutes and proteobacteria.

4. The synthetic auxotroph of claim 3, wherein the organism comprises an *E. coli* strain.

5. The synthetic auxotroph of claim 4, wherein the organism comprises a biosafety strain with an escape frequency of less than $1\times10^{-8}$.

6. The synthetic auxotroph of claim 1, wherein mutation of said one or more mutated essential genes comprises an N or C terminal fusion of a ligand-binding domain that confers post translational, ligand-dependent function to an essential gene product.

7. The synthetic auxotroph of claim 1, wherein mutation of said mutated one or more essential genes comprise a post translationally, ligand-dependent intein domain that imposes a requirement of post-translational, ligand-dependent, intein splicing in order to functionalize the essential gene product.

8. The synthetic auxotroph of claim 1, wherein the ligand-dependent essential genes are genes selected from the group of structural genes, regulatory genes and signaling genes.

\* \* \* \* \*